United States Patent
Monti et al.

(10) Patent No.: US 12,138,075 B2
(45) Date of Patent: Nov. 12, 2024

(54) EAR-WORN HEARING DEVICE

(71) Applicant: Knowles Electronics, LLC, Itasca, IL (US)

(72) Inventors: Christopher L. Monti, Elgin, IL (US); Shehab Albahri, Hanover Park, IL (US); Charles B. King, Oak Park, IL (US); Mohammad Mohammadi, Rolling Meadows, IL (US)

(73) Assignee: Knowles Electronics, LLC, Itasca, IL (US)

( * ) Notice: Subject to any disclaimer, the term of this patent is extended or adjusted under 35 U.S.C. 154(b) by 207 days.

(21) Appl. No.: 17/981,800

(22) Filed: Nov. 7, 2022

(65) Prior Publication Data

US 2024/0148326 A1 May 9, 2024

(51) Int. Cl.
*A61B 5/00* (2006.01)
*H04R 25/00* (2006.01)

(52) U.S. Cl.
CPC .......... *A61B 5/6817* (2013.01); *A61B 5/0059* (2013.01); *H04R 25/603* (2019.05); *H04R 25/604* (2013.01); *H04R 25/609* (2019.05); *H04R 25/652* (2013.01); *A61B 2562/185* (2013.01)

(58) Field of Classification Search
CPC .. H04R 25/603; H04R 25/604; H04R 25/609; H04R 25/652
See application file for complete search history.

(56) References Cited

U.S. PATENT DOCUMENTS

| | | |
|---|---|---|
| 7,822,218 B2 | 10/2010 | Van Halteren |
| 2008/0205679 A1 | 8/2008 | Darbut et al. |
| 2015/0023539 A1 | 1/2015 | Bauman |
| 2016/0199001 A1 | 7/2016 | Lee et al. |
| 2020/0213787 A1 | 7/2020 | Houcek et al. |
| 2022/0225887 A1* | 7/2022 | Goldman ............ A61B 5/02438 |
| 2024/0015450 A1* | 1/2024 | Thielen ................ H04R 1/1041 |

* cited by examiner

*Primary Examiner* — Suhan Ni
(74) *Attorney, Agent, or Firm* — Hickman Becker Bingham Ledesma LLP; Matthew C. Loppnow

(57) ABSTRACT

An ear-worn hearing device including an acoustic transducer and a physiological sensor located between an acoustic sealing flange and an inner end portion of the hearing device is disclosed. The flange can be integrated with the hearing device or be an integral part of a removable ear dome. The flange is configured to form at least a partial seal with the user's ear. The flange can also prevent light from entering into the user's ear canal. A removable ear dome can be located on the hearing device by a portion of the physiological sensor protruding from the housing.

20 Claims, 5 Drawing Sheets

EAR-WORN HEARING DEVICE

FIELD OF THE DISCLOSURE

The present disclosure relates generally to hearing devices and more particularly to hearing devices including one or more physiological sensors and configured for wear over or at least partially in a user's ear canal.

BACKGROUND

Ear-worn hearing devices including an acoustic transducer and a physiological sensor are known generally. U.S. Patent Publication No. 20080205679 discloses an in-ear auditory device coupled to a behind-the-ear (BTE) auxiliary device. The in-ear auditory device comprises a receiver disposed in a housing having an open or closed-ear tip fastened to an end thereof and one or more physiologic sensors affixed to the housing. These and other in-ear physiological sensors however are susceptible to one or more problems, including interference from stray light leaking into the ear canal, improper positioning of the sensor relative to skin tissue in which the physiological condition is detected, and overall size. Thus, there is a desire to provide improved in-ear hearing devices having improved physiological sensors.

BRIEF DESCRIPTION OF THE DRAWINGS

The objects, features and advantages of the present disclosure will become more fully apparent from the following detailed description and the appended claims considered in conjunction with the accompanying drawings. The drawings depict only representative embodiments and are therefore not considered to limit the scope of the disclosure.

Those of ordinary skill in the art will appreciate that the figures are illustrated for simplicity and clarity and therefore may not be drawn to scale and may not include well known features, that the order of occurrence of actions or steps may be different than the order described or the action and steps may be performed concurrently unless specified otherwise, and that the terms and expressions used herein have the meaning understood by those of ordinary skill in the art except where different meanings are attributed to them herein.

DETAILED DESCRIPTION

The disclosure relates generally to hearing devices and more particularly to hearing devices comprising one or more physiological sensors and configured for wear over or at least partially in a user's ear canal. Such hearing devices are referred to herein as "ear-worn hearing devices". Representative hearing devices include but are not limited to receiver-in-canal (RIC), in-the-ear (ITE), completely-in-canal (CIC) hearing devices as well as wired and wireless ear-buds, among other known and future hearing devices.

Such hearing devices generally comprise one or more sound-producing electroacoustic transducers (also referred to herein as an "acoustic transducer" or merely a "transducer") and a physiological sensor integrated with a housing. The transducer can comprise one or more balanced armature receivers alone or in combination with a dynamic speaker, or only a dynamic speaker. The housing comprises an end portion defining a passage terminating at a sound port on an end surface at a distal end of the housing, wherein the housing end portion is configured for wearing on or at least partially in a user's ear canal. A sound output of the one or more transducers is acoustically coupled to the sound port on an end surface of the housing via the passage.

Figure 1:
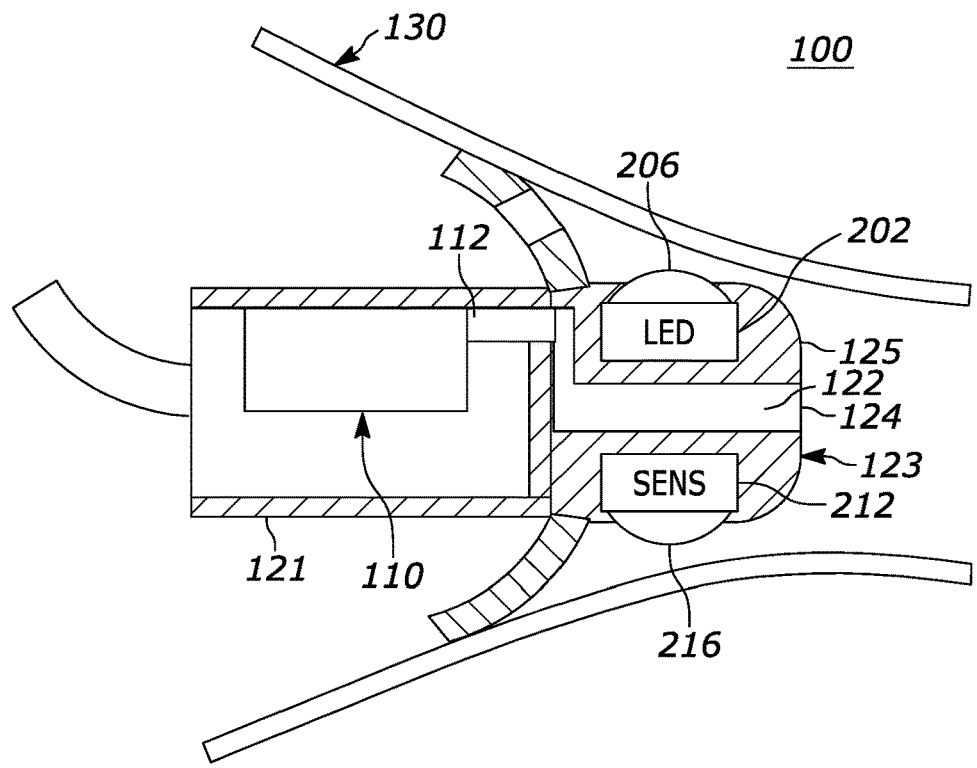
FIG. 1 is a side sectional view of an ear-worn hearing device located partially in a user's ear canal.

In FIG. 1, a hearing device 100 comprises a transducer 110 couple to a housing end portion 123 or disposed at least partially in a housing body portion 121 with a cavity for retaining the transducer. The housing end portion 123 is configured for wear over, or at least partially in, a user's ear canal 130 as described further herein. In FIGS. 1, 2, 4, 6 and 7, a passage or sound conduit 122 extending through the housing end portion 123 acoustically couples a sound output 112 of the transducer to a sound port 124 on an end surface 125 of the housing. In FIG. 1, the transducer 110 is fully encapsulated within a cavity of the housing body portion 121. In other hearing devices however the transducer is only partially disposed within a housing of the hearing device. For example, the housing end portion 123 can be configured (without the body portion 121) as an open-ended sleeve or a cap that extends only partially over a spout or end portion of the transducer from which sound is emitted, wherein a portion of the transducer is uncovered by the housing. The housing portion can be fasted to the transducer with glue or mechanical structure.

The hearing device generally comprises a flange that is part of an ear-dome or integrally formed on the end portion of the housing. The flange can form a partial or full seal with the user's ear. The flange is spaced apart from the distal end of the housing on which the sound port is located. In one implementation, the ear-dome comprises a resilient flange extending from a sleeve portion disposed at least partially about the end portion of the housing. The ear-dome can be permanently affixed to the housing or removably connectable to ear-dome retention structure on the housing end portion. A removable ear-dome permits the end-user to configure the hearing device with ear domes having different sizes and to replace worn or damaged ear-domes. The flange can be opaque to at least partially prevent light from entering into the user's ear canal and interfering with the physiological sensor.

Figure 2:
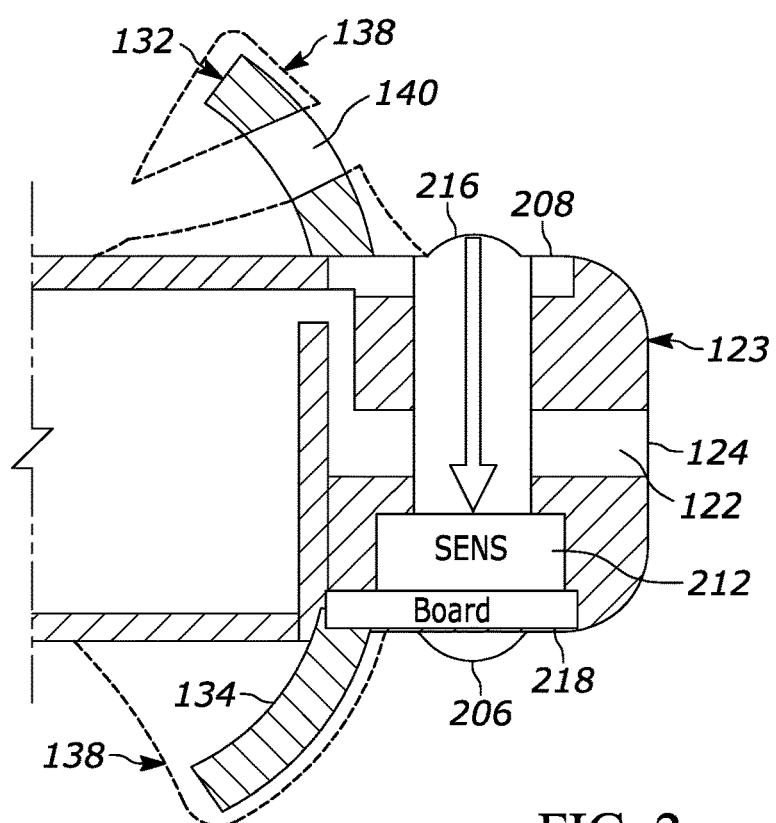
FIG. 2 is a partial side sectional view of an ear-worn hearing device.
Figure 6:
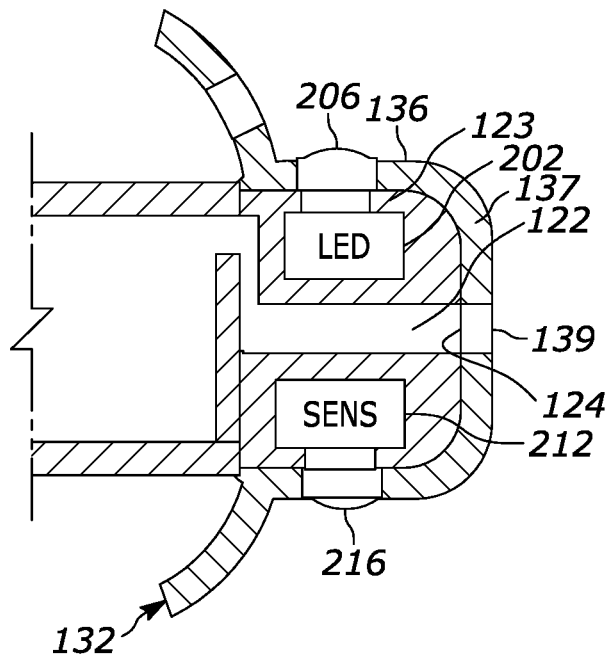
FIG. 6 is a partial side sectional view of another ear-worn hearing device.
Figure 7:
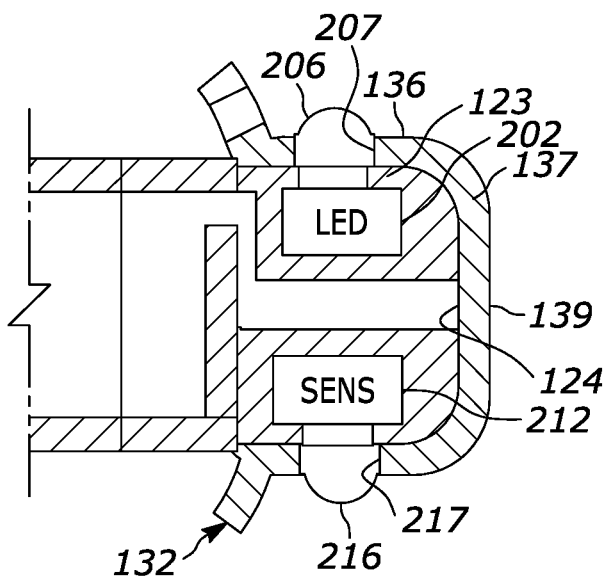
FIG. 7 is a partial side sectional view of another ear-worn hearing device.

In FIG. 2, the ear dome 132 is a discrete unitary member comprising a resilient flange 134 disposed about, and extending outwardly from, the hearing device housing. In FIGS. 6-7, the ear dome 132 flange extends from a cylindrical sleeve or band 136 disposed and retained about the end portion 123 of the housing. Alternatively, the ear dome band can be defined by an inner radial base portion of the flange 134 without the sleeve, as shown in FIG. 2. These and other ear dome configurations can be made from a silicone or other resilient materials. The ear dome can be securely retained on the housing by elastic forces or by structural features that engage the housing. In FIG. 2, the ear dome also comprises a vent 140 to equalize pressure in the ear canal with ambient pressure. The vent may not be required in hearing devices where the ear sealing structure is leaky. Other ear-domes may comprise multiple vents or apertures to permit unobstructed passage of ambient sounds. The vents or apertures can be positioned for optimal light obstruction.

In other implementations, the hearing device comprises a flange integrated with the housing and configured to mount on the user's ear. FIG. 2 shows a flange portion, depicted by dashed lines 138, integrally formed with the housing end portion 123. Representative examples of hearing devices comprising an integral flange include earbuds and ear pieces molded from an impression of the user's ear, among others. The integral flange can be a rigid or resilient member. For example, a resilient flange can be integrally formed on a rigid base portion of an earbud in a two-part molding operation.

The hearing device also comprises one or more physiological sensors integrated with the housing and located between the flange portion and the sound port on the distal end of the hearing device. As described herein, the flange can be part of an ear dome removably fastened to the hearing device housing or the flange can be an integral portion of the hearing device housing. FIGS. 1-2, 4 and 6-7 show portions of the physiological sensor located between the flange portion and the sound port 124 on the end surface or wall (shown at 125 in FIG. 1) of the housing end portion 123.

Figure 8:
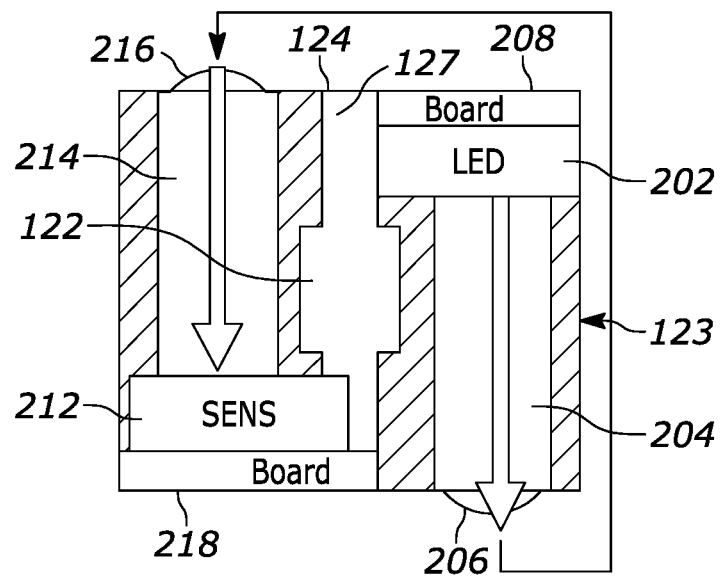
FIG. 8 is a partial sectional end view of another ear-worn hearing device.
Figure 9:
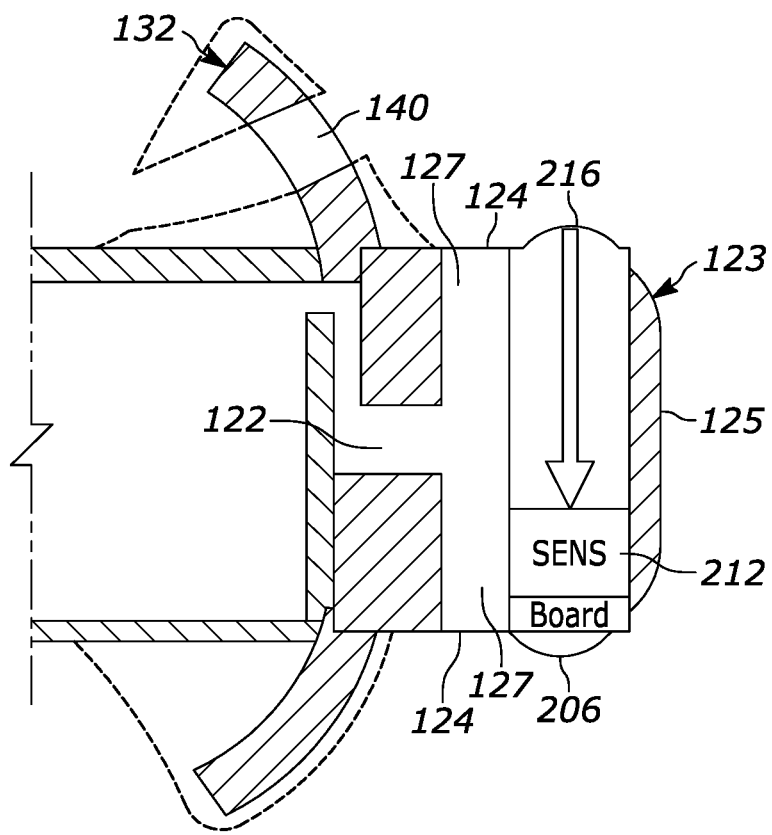
FIG. 9 is a partial side sectional view of an ear-worn hearing device.

In another implementation, the sound passage can terminate at a sound port located on the same surface as the physiological sensor. Alternatively, diverging branches of the sound passage can terminate at one or more sound ports located on the same surfaces as the emitter and receiver. In both implementations, the physiological sensors (e.g., emitter and receiver) and the one or more sound ports are located on a common surface of the housing end portion between the flange and the end wall or surface of the inner end portion of the housing (i.e., the portion of the housing that extends farthest into the user's ear). In FIGS. 8 and 9, for example, the sound conduit 122 includes branches 127 that terminate at corresponding sound ports 124 located on the same surfaces as the emitter 202 and receiver 212. Thus configured, physiological sensor and the one or more sound ports are both located on the flange 134 and the distal end wall or surface 125 of the housing. The sound ports are shown located between physiological sensor and the flange. In other implementations, physiological sensors are located between the flange and the sound ports. In other implementations, the sound conduit 122 can also terminate at a corresponding sound port on the end wall 125.

The physiological sensor generally comprises one or more signal emitters orientated to emit one or more signals from the hearing device and one or more signal receivers orientated to receive one or more signals at the hearing device. The signal emitter can be an LED, laser or other signal source, and the signal receiver can be a sensor capable of detecting the emitter signal. Both the signal emitter and signal receiver are located between the ear-dome flange and the sound port on the end surface of the housing. In one implementation, the signal emitter comprises an emitter waveguide coupled to the signal source and the receiver comprises a receiver waveguide coupled to a signal detector. The emitter waveguide and the receiver waveguide can extend at least partially through the housing. End portions of the emitter waveguide and the receiver waveguide are exposed at a surface of the housing in locations for optimal targeting of tissue for physiological monitoring and for optimal receipt of reflected signals. The emitter waveguide and the receiver waveguide can each include a corresponding lens exposed at one or more surfaces of the housing. The lens can be an integral part of the waveguide or a discrete element assembled with the waveguide. References to the waveguide herein can include the lens or not. Alternatively, one or both the signal emitter and the signal receiver can be located at a surface of the housing or recessed in the housing without the need for the waveguide. A lens can be located directly on or spaced apart from, without an intervening waveguide, each of the signal emitter and the signal receiver. In these implementations, end portions, with or without a lens, of the emitter and receiver waveguides exposed at one or more surfaces of the housing are located between the flange portion of the ear-dome and the sound port on the end surface of the housing.

In FIGS. 1 and 3-7, the hearing device comprises a signal emitter 202 and a signal receiver 212 located in the end portion 123 of the hearing device housing. The signal emitter and receiver can be mounted on a printed circuit board (PCB) and be partially of fully disposed within the housing. Alternatively, the signal emitter and receiver can be disposed or captured within the housing without a PCB and any conductors can be embedded in the housing. In FIGS. 2-5, the signal emitter 202 and signal receiver 212 are mounted on corresponding PCBs 208 and 218, respectively, located on different surfaces of the housing. In other implementations, the signal emitter and receiver can be mounted on a common PCB. In FIGS. 1, 6 and 7, the signal emitter and receiver are embedded in the end portion 123 of the housing without a PCB.

Figure 3:
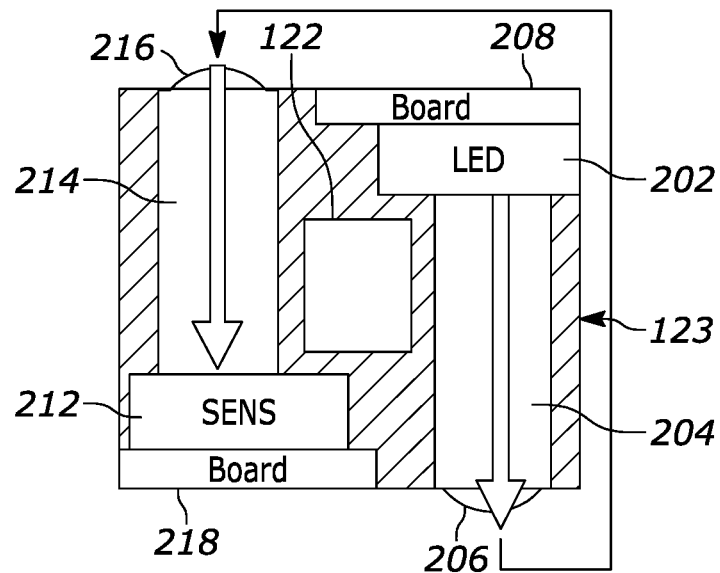
FIG. 3 is a partial sectional end view of an ear-worn hearing device.
Figure 4:
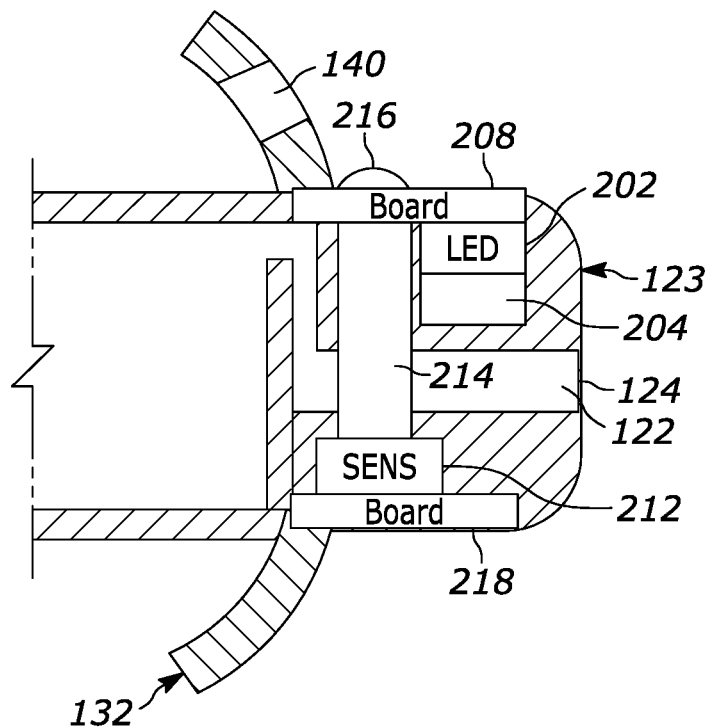
FIG. 4 is a partial side sectional view of another ear-worn hearing device.
Figure 5:
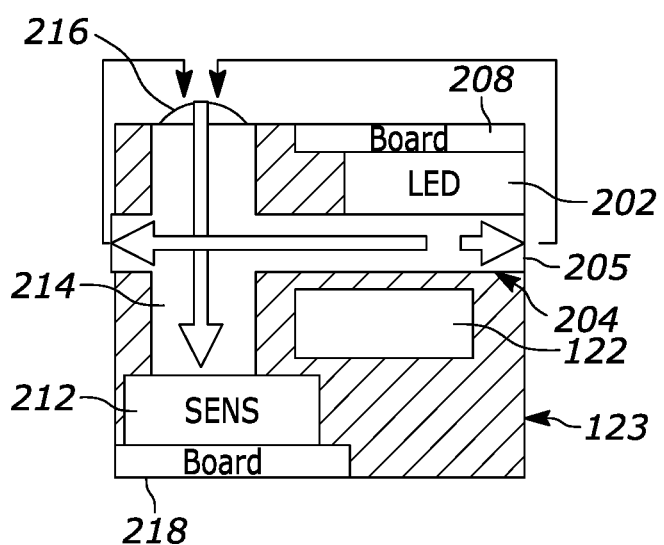
FIG. 5 is sectional end view of the ear-worn hearing device of FIG. 4.

In FIGS. 3-5, an emitter waveguide 204 is coupled to the signal emitter and a receiver waveguide 214 is coupled to the signal receiver. The emitter waveguide and the receiver waveguide can be located on the same side on the sound conduit or on opposite sides of the sound conduit. In FIGS. 2-4, the emitter and receiver waveguides 204 and 214 are on opposite sides of the sound conduit 122.

In FIG. 3, the emitter waveguide includes an emitter lens 206 and the receiver waveguide includes a receiver lens 216. In FIGS. 4-5, the receiver waveguide includes a lens 216 and the emitter waveguide 204 is devoid of a lens. In FIGS. 1, 6 and 7, the signal emitter 202 and the signal receiver 212 are embedded in the housing and coupled directly or indirectly to a corresponding lens 206 and 216, respectively, without an intervening waveguide. In FIGS. 1-7, the one or more lenses protrude from a surface of the housing. In other implementations, the lenses can be flush with a surface of the housing or recessed below the housing surface. In FIG. 5, the emitter waveguide 204 is devoid of a lens, wherein one end 205 of the emitter waveguide is flush with a surface of the housing and another end of the emitter waveguide protrudes slightly from the housing. Thus the ends of the waveguides can be recessed, flush or proud of the housing surface depending on constraints imposed by other structure like an ear-dome or other use-case requirements.

In FIGS. 1-7, the lenses or end surfaces of the waveguides are located or oriented to emit or receive signals in directions perpendicular or non-parallel to a direction in which sound is emitted from the sound port 124 of the hearing device. In other implementations, the lenses or waveguide ends can be located or oriented to emit and receive signals parallel, or parallel and non-parallel, to the direction in which sound is emitted from the sound port. The locations or orientations of the lenses or ends of the waveguides generally depend on the configuration of the hearing device, on the physiological condition to be detected, and space constraints in the ear, among other considerations. For example, a location or orientation for signal emission and detection non-parallel to the direction of sound emission may be preferable for hearing devices configured for partial or full insertion in the ear canal, as shown in FIG. 1. A location or orientation for signal emission and detection parallel to the direction of sound emission may be preferable for hearing devices configured for placement over the ear canal.

The lenses or end surfaces of the waveguides are generally located or oriented to emit signals from, and receive signals at, the same or different surfaces of the hearing device. In hearing devices having a cylindrical housing portion, the lenses or end surfaces of the waveguides can be located on the same or different radial or diametric portions of the housing. In FIGS. 1-3 and 6-7, the emitter lens 206 and the receiver lens 216 are located on opposite sides or surfaces of the housing. In FIG. 3, the emitter and receiver waveguides 204 and 214 are parallel. In FIGS. 4 and 5, emitter and receiver waveguides 204 and 214 are perpendicular to each other. More generally, the waveguides can be arranged non-parallel, either perpendicular or at an angle relative to each other. The receiver lens 216 is located on one surface of the housing and the end 205 from which the emitter signal is emitted is on a different surface of the housing. In FIG. 5, the emitter waveguide 204 extends fully through the housing and the emitter signal emanates from both ends of the emitter waveguide. The emitter waveguide 204 can also include lenses as described herein. More generally, the emitter waveguide can be configured with more than two waveguide branches with or without lenses that extend to corresponding surfaces of the housing. The waveguide branches can be arranged at various angles, e.g., a Y or X configuration, to direct the emitter signal toward tissue in different parts of the ear. Such distribution can compensate for shifting or improper positioning of the hearing device on or in the ear. The receiver waveguide can also have multiple branches with or without lenses extending to surfaces of the housing.

In some implementations, a discrete ear dome is at least partially disposed about a portion of the housing and a portion of the physiological sensor protruding from the housing extends into an aperture of the ear dome. Thus configured, the portion of the physiological sensor protruding from the housing can locate the ear dome on the housing. In some implementations, the portion of the physiological sensor protruding from the housing can also help retain the ear dome on the housing. The ear dome can comprise silicone or some other elastic material that can also help fasten the ear dome to the housing. In some implementations, the ear dome sleeve or band is rigid but sufficiently flexible to permit the ear dome to snap fit into position over the protruding portion(s) of the physiological sensor.

In one implementation, the portion of the physiological sensor protruding from the housing includes end portions of one or more waveguides or lenses of the one or more waveguides. The end portions of the one or more waveguides or the lenses of the one or more waveguides protrude into corresponding recesses or apertures of the ear dome, thereby locating the ear dome on the housing of the hearing device. In FIGS. 6-7, the emitter and receiver lenses 206, 216 or portions of the emitter or receiver waveguides protrude from different portions of the housing and extend into corresponding apertures 207, 217 of the ear dome 132. In other implementations, opposite end portions of the same waveguide that extends fully through the hearing device housing protrude from corresponding portions of the housing. In FIG. 7, the lenses protrude more than the lenses in FIG. 6. In FIG. 5, for example, the emitter waveguide 204 can protrude from opposite sides of the housing and the protruding portions of the waveguide can extend into corresponding apertures of the ear dome.

The ear dome can comprise a flange as described herein and the lenses or end portions of the waveguides protruding from the housing can be located between the flange and the sound port. In some implementations, the ear dome comprises a cover portion having a cover aperture, wherein the cover portion extends over the end portion of the housing and the cover aperture is aligned with the sound port of the hearing device. In FIGS. 6-7, the ear dome 132 comprises an optional cover portion 137 extending from the sleeve portion 136 and disposed over the end portion 123 of the hearing device. An aperture 139 in the cover portion 137 is aligned with the sound port 124 of the hearing device. The ear dome flange can be configured to form at least a partial seal with the user's ear and to reduce light entering into the user's ear canal when the end portion of the housing is at least partially inserted into the user's ear canal.

While the disclosure and what is presently considered to be the best mode thereof has been described in a manner establishing possession and enabling those of ordinary skill in the art to make and use the same, it will be understood and appreciated that there are many equivalents to the representative embodiments described herein and that myriad modifications and variations may be made thereto without departing from the scope and spirit of the invention, which is to be limited not by the embodiments described but by the appended claims and their equivalents.

What is claimed is:

1. An ear-worn hearing device comprising:
    a housing comprising an end portion defining a passage terminating at a sound port on an end surface of the housing, the end portion of the housing configured for wearing over or at least partially in a user's ear canal;
    a sound-producing electroacoustic transducer integrated with the housing, the transducer including a sound output acoustically coupled to the sound port via the passage;
    a physiological sensor integrated with the housing;
    an ear-dome comprising a flange portion on the end portion of the housing, the physiological sensor located between the flange portion and the sound port,
    wherein the ear-dome is configured to at least partially prevent light from entering into the user's ear canal when the end portion of the housing is at least partially inserted into the user's ear canal.

2. The ear-worn hearing device of claim 1, wherein the physiological sensor comprises:
    a signal emitter located between the flange portion of the ear-dome and the sound port on the end surface of the housing; and
    a signal receiver located between the flange portion of the ear-dome and the sound port on the end surface of the housing.

3. The ear-worn hearing device of claim 2, wherein the flange portion of the ear-dome is opaque.

4. The ear-worn hearing device of claim 2, wherein the housing further comprises an ear-dome retention structure, and wherein the ear-dome is removably retained by the ear-dome retention structure.

5. The ear-worn hearing device of claim 2, wherein:
    the signal emitter comprises an emitter waveguide extending at least partially through the housing, an end portion of the emitter waveguide exposed at a surface of the housing and located between the flange portion of the ear-dome and the sound port on the end surface of the housing;

the signal receiver comprises a receiver waveguide extending at least partially through the housing, an end portion of the receiver waveguide exposed at a surface of the housing and located between the flange portion of the ear-dome and the sound port on the end surface of the housing; and the passage of the housing is a sound conduit non-parallel to the emitter waveguide and the receiver waveguide.

6. The ear-worn hearing device of claim 5, wherein the end portion of the emitter waveguide includes an emitter lens exposed at the surface of the housing, and the end portion of the receiver waveguide includes a receiver lens exposed at the surface of the housing.

7. The ear-worn hearing device of claim 5, wherein the emitter waveguide and the receiver wave guide are located on opposite sides of the sound conduit.

8. The ear-worn hearing device of claim 5, wherein the emitter waveguide is non-parallel to the receiver waveguide.

9. The ear-worn hearing device of claim 5, wherein the end portion of the emitter waveguide and the end portion of the receiver waveguide are exposed on different surface portions of the housing.

10. An ear-worn hearing device comprising:
a housing comprising an end portion defining a passage terminating at a sound port on an end surface of the housing, the end portion configured for wearing over or at least partially in a user's ear canal;
a sound-producing electroacoustic transducer integrated with the housing, the transducer including a sound output acoustically coupled to the sound port via the passage;
a physiological sensor integrated with the housing and including a portion protruding from the housing;
an ear-dome comprising a flange extending from a sleeve portion removably disposed at least partially about a portion of the housing, the portion of the physiological sensor protruding from the housing extending into an aperture of the ear dome, wherein the portion of the physiological sensor protruding from the housing locates the ear dome on the housing.

11. The ear-worn hearing device of claim 10, wherein the flange extends outwardly from the sleeve portion, the portion of the physiological sensor protruding from the housing includes end portions of one or more waveguides, or lenses of one or more waveguides, located between the flange and the sound port on the end surface of the housing, and wherein the end portions of the one or more waveguides or the lenses of the one or more waveguides protrude into corresponding apertures of the sleeve portion.

12. The ear-worn hearing device of claim 11, wherein the ear dome comprises a cover portion having a cover aperture, and wherein the cover portion extends over the end surface of the housing and the cover aperture is aligned with the sound port.

13. The ear-worn hearing device of claim 11, wherein the flange of the ear-dome is configured to form at least a partial seal with the user's ear and to reduce light entering into the user's ear canal when the ear-worn hearing device is worn by a user.

14. The ear-worn hearing device of claim 10, wherein the physiological sensor comprises:
a signal emitter including an emitter waveguide extending at least partially through the housing, an end portion of the emitter waveguide protruding from a surface of the housing and at least partially into a first aperture of the sleeve portion; and
a signal receiver including a receiver waveguide extending at least partially through the housing, an end portion of the receiver waveguide protruding from a surface of the housing and at least partially into a second aperture of the sleeve portion,
wherein the portion of the physiological sensor protruding from the housing comprises the end portion of the emitter waveguide and the end portion of the receiver waveguide.

15. The ear-worn hearing device of claim 14, wherein the end portion of the emitter waveguide and the end portion of the receiver waveguide protrude from different surface portions of the housing.

16. An ear-worn hearing device comprising:
a housing including an inner end portion configured for wearing at least partially in a user's ear;
a sound-producing electroacoustic transducer integrated with the housing;
a sound conduit acoustically coupling a sound output of the transducer to a sound port on an end wall of the inner end portion of the housing;
a flange integrally formed with the housing and configured to mount on the user ear, the flange extending away from the housing;
a physiological sensor comprising a signal emitter and a signal receiver located on the inner end portion of the housing,
wherein the physiological sensor is located between the flange and the sound port.

17. The ear-worn hearing device of claim 16,
wherein the signal emitter includes an emitter waveguide extending at least partially through the housing,
wherein the signal receiver includes a receiver waveguide extending at least partially through the housing, and
wherein the sound conduit is non-parallel to the emitter waveguide and the receiver waveguide.

18. The ear-worn hearing device of claim 17, wherein an end of the emitter waveguide includes an emitter lens exposed at a surface of the housing, and an end of the receiver waveguide including a receiver lens exposed at a surface of the housing, and wherein the signal emitter emits a signal from a first portion of the housing and the signal receiver receives a signal from a second portion of the housing different than the first portion.

19. The ear-worn hearing device of claim 18, wherein the emitter waveguide is non-parallel to the receiver waveguide.

20. The ear-worn hearing device of claim 18, wherein the flange is configured to form at least a partial seal with the user's ear and to reduce light entering into the user's ear canal when the ear-worn hearing device is worn by a user.

\* \* \* \* \*